(12) United States Patent
Nishino et al.

(10) Patent No.: US 7,932,400 B2
(45) Date of Patent: Apr. 26, 2011

(54) PROCESS FOR PREPARING IMIDAZOLIDIN-2,4-DIONE COMPOUND AND METHOD FOR ACQUIRING SOLID STATE 4,5-DIHYDROXY-2-IMIDAZOLIDINONE COMPOUND

(75) Inventors: Shigeyoshi Nishino, Ube (JP); Hidetaka Shima, Ube (JP); Tetsuro Shimano, Ube (JP); Kimihiko Yoshimura, Ube (JP)

(73) Assignee: Ube Industries, Ltd., Ube-shi (JP)

( * ) Notice: Subject to any disclaimer, the term of this patent is extended or adjusted under 35 U.S.C. 154(b) by 8 days.

(21) Appl. No.: 12/373,548

(22) PCT Filed: Jul. 13, 2007

(86) PCT No.: PCT/JP2007/063955
§ 371 (c)(1),
(2), (4) Date: Jan. 13, 2009

(87) PCT Pub. No.: WO2008/007763
PCT Pub. Date: Jan. 17, 2008

(65) Prior Publication Data
US 2010/0010233 A1    Jan. 14, 2010

(30) Foreign Application Priority Data

Jul. 14, 2006 (JP) ................. 2006-193806
Nov. 22, 2006 (JP) ................. 2006-316144
Mar. 7, 2007 (JP) ................. 2007-057747
Mar. 27, 2007 (JP) ................. 2007-081891

(51) Int. Cl.
*C07D 233/74* (2006.01)
*C07D 233/40* (2006.01)

(52) U.S. Cl. ................. 548/317.1; 548/317.5
(58) Field of Classification Search ............. 548/317.1, 548/317.5; 514/389, 392
See application file for complete search history.

(56) References Cited

U.S. PATENT DOCUMENTS 6,103,898 A    8/2000    Kramer et al.

FOREIGN PATENT DOCUMENTS

| JP | 57-124728 A | 8/1982 |
|---|---|---|
| JP | 11-158155 A | 6/1999 |
| JP | 2000-160351 A | 6/2000 |
| JP | 2006-192114 A | 7/2006 |

OTHER PUBLICATIONS

Sigachev et al, Journal of Heterocyclic Chemistry (2006), vol. 43(5), pp. 1295-1302.*
Fisher et al., "The Glyoxalines I Some Hydantoins Resulting from the Reaction between Phenylglyoxal and Urea and Substituted Ureas". Journal of the American Chemical Society, vol. 64, 1942, pp. 1434-1436.
Nematollahi, et al., "New Compounds: Synthesis of 1-Aryi Substituted Hydantoins".Journal of Pharmaceutical Sciences. vol. 62, No. 2, Feb. 1973, pp. 340-341.
Berni et al., "Solvent Finishing of Cotton and Cotton-Polyester Blends" Part I: Binary Aqueous Azeotropes as Solvents for Dimethyloidlhydroxyethyleneurea, Textile Research Journal, vol. 45, No. 5, May 1975, pp. 421-425.
Vail, et al., "Formation and Identification of cis- and trans-Dihydroxyimidazolidinones from Ureas and Glyoxal", Journal of Organic Chemistry, vol. 30, No. 7, Jul. 1965, pp. 2179-2182.
Chinese Application No. 200780026643.1, Chinese Office Action, Oct. 12, 2010, pp. 1-6.

* cited by examiner

*Primary Examiner* — Kamal A Saeed
*Assistant Examiner* — Kristin Bianchi
(74) *Attorney, Agent, or Firm* — Birch, Stewart, Kolasch & Birch, LLP

(57) ABSTRACT

An object of the present invention is to provide an industrially suitable process for preparing an imidazolidin-2,4-dione compound which is safe, simple and easy to prepare the imidazolidin-2,4-dione compound with high yield, which is a useful compound, for example, as a material for decomposing a harmful halogenated aromatic hydrocarbon compound such as dioxin, etc., an electroless silver plating solution for electronic parts, or a diazo copying material, etc. This object can be solved by a process for preparing an imidazolidin-2,4-dione compound which comprises subjecting a 4,5-dihydroxy-2-imidazolidinone compound, (1) to dehydration reaction in the presence of an acid catalyst(s); or (2) to reaction at 100 to 300° C. Or, it can be solved by a process for preparing an imidazolidin-2,4-dione compound which comprises reacting a mixed solution of a urea compound, glyoxal, and a base at 20 to 300° C.

Also, an object of the present invention is to provide a method for acquiring a 4,5-dihydroxy-2-imidazolidinone from an aqueous solution containing a 4,5-dihydroxy-2-imidazolidinone by a simple and easy method. This object can be solved by a process for acquiring a solid state 4,5-dihydroxy-2-imidazolidinone compound which comprises mixing an organic solvent with an aqueous solution containing a 4,5-dihydroxy-2-imidazolidinone compound, and subjecting the mixture to azeotropic distillation.

15 Claims, No Drawings

PROCESS FOR PREPARING IMIDAZOLIDIN-2,4-DIONE COMPOUND AND METHOD FOR ACQUIRING SOLID STATE 4,5-DIHYDROXY-2-IMIDAZOLIDINONE COMPOUND

TECHNICAL FIELD

The present invention relates to a process for preparing an imidazolidin-2,4-dione compound.

The present invention also relates to a method for acquiring a solid state 4,5-dihydroxy-2-imidazolidinone compound from an aqueous solution containing a 4,5-dihydroxy-2-imidazolidinone compound.

BACKGROUND ART

The imidazolidin-2,4-dione compound is a compound useful for, for example, a material for decomposing a harmful halogenated aromatic hydrocarbon compound such as dioxin, etc. (for example, see Patent Literature 1), an electroless silver plating solution for electronic parts (for example, see Patent Literature 2) or a diazo copying material (for example, see Patent Literature 3), etc.

There has been disclosed a method for producing 1,3-dimethyl-imidazolidin-2,4-dione by reacting 1,3-dimethyl-4,5-dihydroxy-2-imidazolidinone and formic acid under reflux (for example, see Patent Literature 4). However, according to this method, it needs to use a large amount of formic acid which is harmful to skin or eyes, and causes bad effects on a living body such as liver, kidney, etc., by chronic exposure. Moreover, the treatment after the reaction is complicated, so that there were problems on working procedure and production as an industrial manufacturing method of an imidazolidin-2,4-dione compound.

Also, the above-mentioned 1,3-dimethyl-4,5-dihydroxy-2-imidazolidinone is useful as a synthetic intermediate or a starting material for medicines and agricultural chemicals other than for the preparation of the 1,3-dimethyl-imidazolidin-2,4-dione.

As a preparation method of the compound, a method of reacting glyoxal and 1,3-dimethylurea in water in the presence of a base to obtain an aqueous solution of 4,5-dihydroxy-1,3-dimethyl-2-imidazolidinone, and removing water from the aqueous solution to isolate 4,5-dihydroxy-1,3-dimethyl-2-imidazolidinone has conventionally been disclosed (for example, see Non-Patent Literature 1). However, distillation of water accompanies danger in bumping, etc., and a huge amount of heat energy is required due to large specific heat of water, whereby it was not a satisfactory method as an industrially practical method.

Patent Literature 1: JP 2006-192114A
Patent Literature 2: JP 2000-160351A
Patent Literature 3: JP 57-124728A
Patent Literature 4: JP 11-158155A
Non-Patent Literature 1: J. Org. Chem., 30, 2179 (1965)

DISCLOSURE OF THE INVENTION

Problems to be Solved by the Invention

An object of the present invention is to solve the above-mentioned problem(s), and to provide an industrially suitable process for preparing an imidazolidin-2,4-dione compound which is safe, simply and easy to prepare the imidazolidin-2,4-dione compound with high yield (Problem 1).

Another object of the present invention is to solve the above-mentioned problem(s), and to provide a method for acquiring a solid state 4,5-dihydroxy-2-imidazolidinone compound from an aqueous solution containing the 4,5-dihydroxy-2-imidazolidinone compound by a simple and easy procedure (Problem 2).

The above-mentioned problem 1 of the present invention has been solved by a process (hereinafter also referred to as "Method 1") for preparing an imidazolidin-2,4-dione compound represented by the formula (2):

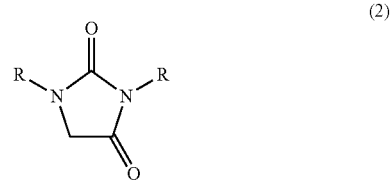

(2)

(wherein R represents a hydrogen atom or a hydrocarbon group.)
which comprises subjecting a 4,5-dihydroxy-2-imidazolidinone compound represented by the formula (1):

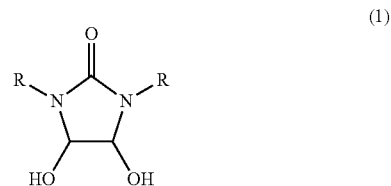

(1)

(wherein R has the same meaning as defined above.)
(A) to dehydration reaction in the presence of an acid catalyst(s); or
(B) to reaction at 100° C. to 300° C.

Or, the above-mentioned problem 1 of the present invention can be also solved by a process (hereinafter also referred to as "Method 2") for preparing the above-mentioned imidazolidin-2,4-dione compound represented by the formula (2), which comprises reacting a mixed solution containing a urea compound represented by the formula (3):

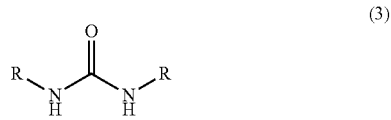

(3)

(wherein R has the same meaning as defined above.), glyoxal and a base at 20 to 300° C.

The above-mentioned problem 2 of the present invention can be solved by the method of acquiring a solid state 4,5-dihydroxy-2-imidazolidinone compound represented by the formula (1):

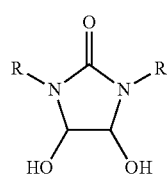

(1)

(wherein R represents a hydrogen atom or a hydrocarbon group.)
which comprises mixing an organic solvent with an aqueous solution containing a 4,5-dihydroxy-2-imidazolidinone compound represented by the formula (1), and subjecting the mixture to azeotropic distillation.

According to the present invention, an industrially suitable process for preparing an imidazolidin-2,4-dione compound, which is safe, simple and easy to prepare the imidazolidin-2,4-dione compound with high yield, can be provided.

Also, according to the present invention, a method for acquiring a solid state 4,5-dihydroxy-2-imidazolidinone compound from an aqueous solution containing the 4,5-dihydroxy-2-imidazolidinone compound by a simple and easy procedure can be provided. This solid state 4,5-dihydroxy-2-imidazolidinone compound can be used in the above-mentioned Method 1 as the 4,5-dihydroxy-2-imidazolidinone compound represented by the formula (1)

BEST MODE TO CARRY OUT THE INVENTION

The 4,5-dihydroxy-2-imidazolidinone compound to be used in the present invention is represented by the above-mentioned formula (1). Also, the urea compound to be used in the present invention is represented by the above-mentioned formula (3). In these formulae (1) and (3), R represents a hydrogen atom or a hydrocarbon group. As the hydrocarbon group, there may be mentioned, for example, a linear alkyl group having 1 to 6 carbon atoms such as methyl group, ethyl group, propyl group, butyl group, pentyl group, hexyl group, etc.; a branched alkyl group having 3 to 6 carbon atoms such as 2-propyl group, 2-butyl group, etc.; a cycloalkyl group having 3 to 6 carbon atoms such as cyclopropyl group, cyclobutyl group, cyclopentyl group, cyclohexyl group, etc.; an aralkyl group having 7 to 12 carbon atoms such as benzyl group, phenethyl group, phenylpropyl group, etc.; and an aryl group having 6 to 20 carbon atoms such as phenyl group, tolyl group, biphenylyl group, naphthyl group, etc. These groups contain various kinds of isomers.

As the acid catalyst used in the step (A) of the above-mentioned Method 1, there may be exemplified by at least one acid selected from the group consisting of a sulfonic acid, a hydrogen halide, a halogenated carboxylic acid, clay minerals, sulfonic acid type cation exchange resin, fluorinated sulfonic acid resin; silica-alumina and inorganic oxides, and there may be mentioned, for example, a sulfonic acid such as sulfuric acid, methanesulfonic acid, benzenesulfonic acid, p-toluenesulfonic acid, trifluoromethanesulfonic acid, etc.; a hydrogen halide such as hydrochloric acid, hydrobromic acid, hydroiodic acid, etc.; a halogenated carboxylic acid such as trifluoroacetic acid, trichloroacetic acid, etc.; a clay mineral such as acid clay, etc.; a sulfonic acid type cation exchange resin such as AMBERLITE (trade name), DOWEX (trade name), DIAION (trade name), DENIOLITE (trade name), LEWATIT (trade name), SUMIKAION (trade name), etc.; a fluorinated sulfonic acid resin such as NAFION (trade name), etc.; an inorganic oxide such as silica-alumina, zeolite, vanadium oxide, etc., preferably a sulfonic acid, a sulfonic acid type cation exchange resin and an inorganic oxide are used. These acid catalysts may be used solely or as the mixture of two or more kinds.

An amount of the acid catalyst to be used in the step (A) of the above-mentioned Method 1 is preferably 0.01 to 1000 mg, more preferably 0.1 to 500 mg based on 1 g of the 4,5-dihydroxy-2-imidazolidinone compound.

The dehydration reaction of the step (A) of the above-mentioned Method 1 is carried out in the presence or in the absence of a solvent. As the solvent to be used, it is not specifically limited so long as it does not disturb the reaction, and there may be mentioned, for example, water; an alcohol such as methanol, ethanol, isopropyl alcohol, t-butyl alcohol, ethylene glycol, triethylene glycol, etc.; an amide such as N,N-dimethylformamide, N,N-dimethylacetamide, N-methylpyrrolidone, etc.; a urea such as N,N'-dimethylimidazolidinone, etc.; an ether such as diethyl ether, diisopropyl ether, tetrahydrofuran, dioxane, etc.; an aromatic hydrocarbon such as benzene, toluene, xylene, etc.; a carboxylic acid ester such as ethyl acetate, propyl acetate, butyl acetate, etc., preferably water, a urea and an ether are used. These solvents may be used solely or as the mixture of two or more kinds.

An amount of the solvent to be used in the step (A) of the above-mentioned Method 1 may be optionally controlled depending on a degree of uniformity or condition of stirring of the reaction mixture, and preferably 0 to 100 g, more preferably 0.1 to 50 g, particularly preferably 0.2 to 50 g based on 1 g of the 4,5-dihydroxy-2-imidazolidinone compound.

The step (A) of the above-mentioned Method 1 is carried out, for example, by means of mixing a 4,5-dihydroxy-2-imidazolidinone compound, an acid catalyst and a solvent and stirring the mixture, etc. On this occasion, a reaction temperature is preferably 0 to 300° C., more preferably 20 to 250° C.

The reaction of the step (B) of the above-mentioned Method 1 is desirably carried out in the presence of a solvent, and, for example, it can be carried out in the solvent at the initial stage of the reaction. As the solvent to be used, it is not specifically limited so long as it does not disturb the reaction, and there may be mentioned, for example, water; an alcohol such as methanol, ethanol, isopropyl alcohol, t-butyl alcohol, ethylene glycol, triethylene glycol, etc.; an amide such as N,N-dimethylformamide, N,N-dimethylacetamide, N-methylpyrrolidone, etc.; a urea such as N,N'-dimethylimidazolidinone, etc.; an ether such as diethyl ether, diisopropyl ether, tetrahydrofuran, dioxane, etc.; an aromatic hydrocarbon such as benzene, toluene, xylene, etc.; a carboxylic acid ester such as ethyl acetate, propyl acetate, butyl acetate, etc., preferably water, a urea and an ether, more preferably water is used. These solvents may be used solely or as the mixture of two or more kinds.

An amount of the solvent to be used in the step (B) of the above-mentioned Method 1 may be optionally controlled depending on a degree of uniformity or condition of stirring of the reaction mixture, and preferably 0 to 100 g, more preferably 0 to 50 g based on 1 g of the 4,5-dihydroxy-2-imidazolidinone compound.

The step (B) of the above-mentioned Method 1 is carried out, for example, by means of mixing a 4,5-dihydroxy-2-imidazolidinone compound and a solvent and stirring the mixture, etc. On this occasion, a reaction temperature is preferably 100 to 300° C., more preferably 150 to 250° C.

Incidentally, the 4,5-dihydroxy-2-imidazolidinone compound used in the above-mentioned Method 1 may be a compound obtained by subjecting a urea compound represented by the formula (3):

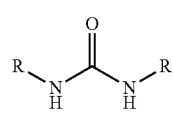

(3)

(wherein R has the same meaning as defined above.)
and glyoxal to condensation reaction in the presence of a base.

An amount of the glyoxal to be used in the above-mentioned condensation reaction is preferably 0.9 to 1.4 mol, more preferably 1.0 to 1.3 mol based on 1 mol of the urea compound.

As the base to be used in the above-mentioned condensation reaction, there may be mentioned, for example, an alkali metal hydroxide such as sodium hydroxide, potassium hydroxide, etc.; an alkali metal carbonate such as sodium carbonate, potassium carbonate, etc.; an alkali metal hydrogen carbonate such as sodium hydrogen carbonate, potassium hydrogen carbonate, etc.; an alkali metal alkoxide such as sodium methoxide, potassium methoxide, etc.; an organic base such as triethylamine, diisopropylethylamine, pyridine, picoline, etc., preferably an organic base and an alkali metal hydroxide are used. These bases may be used solely or as the mixture of two or more kinds.

An amount of the base to be used in the above-mentioned condensation reaction is not particularly limited so long as it is such an amount that a pH of the reaction mixture can be controlled preferably to 7 to 14, more preferably 8 to 13.

The above-mentioned condensation reaction is desirably carried out in the presence of a solvent. As the solvent to be used, it is not particularly limited so long as it does not disturb the reaction, and there may be mentioned, for example, water; an alcohol such as methanol, ethanol, isopropyl alcohol, t-butyl alcohol, ethylene glycol, triethylene glycol, etc.; an amide such as N,N-dimethylformamide, N,N-dimethylacetamide, N-methylpyrrolidone, etc.; a urea such as N,N'-dimethylimidazolidinone, etc.; a sulfoxide such as dimethyl sulfoxide, etc.; an ether such as diethyl ether, diisopropyl ether, tetrahydrofuran, dioxane, etc.; an aromatic hydrocarbon such as benzene, toluene, xylene, etc.; a carboxylic acid ester such as ethyl acetate, propyl acetate, butyl acetate, etc., preferably water is used. These solvents may be used solely or as the mixture of two or more kinds.

An amount of the solvent to be used in the above-mentioned condensation reaction may be optionally controlled depending on a degree of uniformity or condition of stirring of the reaction mixture, and preferably 1 to 100 g, more preferably 2 to 50 g based on 1 g of the urea compound.

The above-mentioned condensation reaction is carried out, for example, by a method of mixing a urea compound, glyoxal, a base and a solvent, controlling a pH of the reaction mixture preferably to 7 to 14, more preferably to 8 to 13, and stirring the mixture, etc. On this occasion, a reaction temperature at that time is preferably 0 to 300° C., more preferably 20 to 200° C., and a reaction pressure is not particularly limited.

The 4,5-dihydroxy-2-imidazolidinone compound obtained by the above-mentioned condensation reaction may be isolated and purified by a conventional method, for example, neutralization, extraction, filtration, condensation, distillation, recrystallization, crystallization, column chromatography, etc., after completion of the reaction, but it may be used as a solution of the 4,5-dihydroxy-2-imidazolidinone compound in the Method 1 without specifically carrying out isolation and purification as such or after controlling a content thereof by condensation, etc.

In the present invention, as mentioned above, the imidazolidin-2,4-dione compound can be prepared by successively carrying out the step of subjecting the urea compound and glyoxal to condensation reaction in the presence of a base to obtain a 4,5-dihydroxy-2-imidazolidinone compound, and then, a step of subjecting the obtained 4,5-dihydroxy-2-imidazolidinone compound (1) to dehydration reaction in the presence of an acid catalyst(s), or (2) to reaction at 100° C. to 300° C., to obtain an imidazolidin-2,4-dione compound, without isolating the 4,5-dihydroxy-2-imidazolidinone compound in the course of the reaction. On this occasion, the reaction conditions are the same as mentioned above.

Or, even when the above-mentioned Method 2 is used, the imidazolidin-2,4-dione compound can be prepared without isolating the 4,5-dihydroxy-2-imidazolidinone compound in the course of the reaction.

As a preferred embodiment of the reaction of the above-mentioned Method 2, there may be mentioned to carry out the reaction by adding a urea compound to a mixed solution of glyoxal and a base. At this time, the mixed solution of glyoxal and the base is preferably a basic.

An amount of the glyoxal to be used in the above-mentioned Method 2 is preferably 0.9 to 1.5 mol, more preferably 1.0 to 1.3 mol based on 1.0 mol of the urea compound.

As the base to be used in the reaction of the above-mentioned Method 2, there may be mentioned, for example, a hydroxide of an alkali metal such as sodium hydroxide, potassium hydroxide, etc.; a carbonate of an alkali metal such as sodium carbonate, potassium carbonate, etc.; a hydrogen carbonate of an alkali metal such as sodium hydrogen carbonate, potassium hydrogen carbonate, etc.; an alkoxide of an alkali metal such as sodium methoxide, potassium methoxide, etc.; and an organic base such as triethylamine, diisopropylethylamine, pyridine, picoline, etc., preferably an organic base, a hydroxide of an alkali metal, more preferably an organic base, particularly preferably an alkyl amine such as triethylamine, diisopropylethylamine, etc., are used. These bases may be used solely or as the mixture of two or more kinds.

An amount of the base to be used in the above-mentioned Method 2 is not specifically limited so long as it is such an amount that a pH of the mixed solution becomes preferably a pH of 7 to 14, more preferably a pH of 8 to 13.

The reaction of the above-mentioned Method 2 is desirably carried out in the presence of a solvent. As the solvent to be used, it is not particularly limited so long as it does not disturb the reaction, and there may be mentioned, for example, water; an alcohol such as methanol, ethanol, isopropyl alcohol, t-butyl alcohol, ethylene glycol, triethylene glycol, etc.; an amide such as N,N-dimethylformamide, N,N-dimethylacetamide, N-methylpyrrolidone, etc.; a urea (provided that those which react with glyoxal are excluded) such as N,N'-dimethylimidazolidinone, etc.; an ether such as diethyl ether, diisopropyl ether, tetrahydrofuran, dioxane, etc.; an aromatic hydrocarbon such as benzene, toluene, xylene, etc.; a carboxylic acid ester such as ethyl acetate, propyl acetate, butyl acetate, etc., preferably water and an ether, more preferably water is used. These solvents may be used solely or as the mixture of two or more kinds.

An amount of the solvent to be used in the above-mentioned Method 2 may be optionally controlled depending on a degree of uniformity or condition of stirring of the reaction mixture, and preferably 0.1 to 100 g, more preferably 0.2 to 50 g based on 1 g of the urea compound.

The above-mentioned Method 2 is carried out, for example, by reacting a mixed solution of a urea compound, glyoxal and a base preferably at 20 to 300° C., more preferably at 150 to 250° C. On this occasion, a reaction pressure is not particularly limited.

In case of using an organic base as a base and water as a solvent, it is desired to carry out the reaction while removing the organic base and water by distillation.

As a preferred embodiment of the reaction of the above-mentioned Method 2, there may be mentioned a method in which a urea compound is added to a basic mixed solution comprising glyoxal and an organic base while a temperature of the solution is maintained to 20 to 80° C., subsequently the temperature is raised to 150° C. to 250° C. to carry out the reaction. Incidentally, at that time, it is desired to carry out the reaction while removing the organic base and water by distillation.

The imidazolidin-2,4-dione compound obtained by the present invention may be isolated and purified by a conventional method, for example, neutralization, extraction, filtration, condensation, distillation, recrystallization, crystallization, column chromatography, etc., after completion of the reaction.

The organic solvent to be used in the above-mentioned acquiring method of the solid state 4,5-dihydroxy-2-imidazolidinone compound is not particularly limited so long as it forms an azeotropic mixture (that is, an organic solvent which is azeotropically distilled with water) of the organic solvent and water preferably under 1 to 100 kPa at 30 to 130° C., more preferably under 5 to 100 kPa at 50 to 100° C., and is inactive to 4,5-dihydroxy-2-imidazolidinone. As such organic solvent, there may be mentioned, for example, an aliphatic alcohol such as ethanol, n-propyl alcohol, isopropyl alcohol, n-butyl alcohol, 2-butyl alcohol, isobutyl alcohol, t-butyl alcohol, allyl alcohol, cyclohexanol, benzyl alcohol, etc.; an aromatic alcohol such as phenol, cresol, etc.; an aliphatic hydrocarbon such as n-pentane, n-hexane, n-heptane, cyclohexane, etc.; a halogenated aliphatic hydrocarbon such as methylene chloride, chloroform, carbon tetrachloride, 1,2-dichloroethylene, trichloroethylene, 1-chloropropane, 2-chloropropane, 1,2-dichloropropane, 1,4-dichlorobutane, etc.; a nitrated aliphatic hydrocarbon such as nitromethane, etc.; an aromatic hydrocarbon such as benzene, toluene, xylene, ethylbenzene, isoproylbenzene, butylbenzene, cyclohexylbenzene, tetralin, naphthalene, etc.; a halogenated aromatic hydrocarbon such as monochlorobenzene, o-dichlorobenzene, monochloronaphthalene, etc.; a nitrated aromatic hydrocarbon such as nitrobenzene, etc.; an ether such as diethyl ether, diisopropyl ether, dibutyl ether, 1,2-dimethoxyethane, dioxane, trioxane, epichlorihydrin, anisole, diphenyl ether, ethyleneglycol dimethyl ether, ethyleneglycol diethyl ether, ethyleneglycol dibutyl ether, diethyleneglycol dimethyl ether, etc.; an ester such as propyl formate, butyl formate, ethyl acetate, propyl acetate, butyl acetate, phenyl acetate, benzyl acetate, methyl propionate, ethyl propionate, methyl chloroacetate, methyl butyrate, ethyl butyrate, propyl butyrate, methyl isobutyrate, ethyl isobutyrate, propyl isobutyrate, methyl caproate, methyl benzoate, ethyl benzoate, propyl benzoate, methyl cinnamate, diethyl carbonate, methyl acrylate, etc.; a nitrile such as acetonitrile, propionitrile, adiponitrile, benzonitrile, acrylonitrile, etc.; an amine such as pyridine, piperidine, methylpyridine, nicotine, etc., preferably an aromatic hydrocarbon and an ester are used.

These solvents may be used solely or as the mixture of two or more kinds.

An amount of the organic solvent to be used in the above-mentioned acquiring method is preferably 1 to 100 ml, more preferably 5 to 50 ml based on 1 g of the 4,5-dihydroxy-2-imidazolidinone compound.

The above-mentioned acquiring method may be carried out, for example, in such a procedure that an organic solvent is mixed with an aqueous solution containing the 4,5-dihydroxy-2-imidazolidinone compound in an atmosphere of an inert gas, and then water is removed by azeotropic distillation preferably under 1 to 100 kPa at 30 to 130° C., more preferably under 5 to 100 kPa at 50 to 100° C., etc.

Incidentally, the aqueous solution containing the 4,5-dihydroxy-2-imidazolidinone compound used in the above-mentioned acquiring method can be obtained, for example, by reacting a urea compound and glyoxal in the presence of a base (for example, described as Reference example 1). Also, the above-mentioned aqueous solution may contain a compound (for example, a urea compound, glyoxal and a base used in synthesis of the 4,5-dihydroxy-2-imidazolidinone compound) which does not participate in the azeotropic distillation.

As the base to be used in the above-mentioned synthesis of the aqueous solution containing the 4,5-dihydroxy-2-imidazolidinone compound, there may be mentioned, for example, an alkali metal hydroxide such as sodium hydroxide, potassium hydroxide, etc.; an alkali metal carbonate such as sodium carbonate, potassium carbonate, etc.; an alkali metal hydrogen carbonate such as sodium hydrogen carbonate, potassium hydrogen carbonate, etc.; an alkali metal alkoxide such as sodium methoxide, potassium methoxide, etc.; an organic base such as triethylamine, diisopropylethylamine, tributylamine, picoline, pyridine etc., preferably an organic base, more preferably triethylamine, diisopropylethylamine, tributylamine and pyridine are used. These bases may be used solely or as the mixture of two or more kinds.

An amount of the base to be used in the above-mentioned synthesis of the aqueous solution containing the 4,5-dihydroxy-2-imidazolidinone compound is not particularly limited so long as it is such an amount that a pH of the reaction mixture can be controlled preferably to 7 to 14, more preferably to 8 to 13.

The above-mentioned synthesis of the aqueous solution containing the 4,5-dihydroxy-2-imidazolidinone compound can be carried out in the absence of or in the presence of a solvent. As the solvent to be used, it is not particularly limited so long as it does not disturb the reaction, and there may be mentioned, for example, water; an alcohol such as methanol, ethanol, isopropyl alcohol, t-butyl alcohol, ethylene glycol, triethylene glycol, etc.; an amide such as N,N-dimethylformamide, N,N-dimethylacetamide, N-methylpyrrolidone, etc.; a urea such as N,N'-dimethylimidazolidinone, etc.; a sulfoxide such as dimethyl sulfoxide, etc.; an ether such as diethyl ether, diisopropyl ether, tetrahydrofuran, dioxane, etc.; an aromatic hydrocarbon such as benzene, toluene, xylene, etc.; a carboxylic acid ester such as ethyl acetate, propyl acetate, butyl acetate, etc. These solvents may be used solely or as the mixture of two or more kinds.

An amount of the solvent to be used in the above-mentioned synthesis of the aqueous solution containing the 4,5-dihydroxy-2-imidazolidinone compound may be optionally controlled depending on a degree of uniformity or condition of stirring of the reaction mixture, and preferably 1 to 100 g, more preferably 2 to 50 g based on 1 g of the urea compound.

The above-mentioned synthesis of the aqueous solution containing the 4,5-dihydroxy-2-imidazolidinone compound can be carried out, for example, by a method in which a urea compound, a dicarbonyl compound, a base and a solvent are mixed, a pH of the reaction mixture is adjusted preferably to 7 to 14, more preferably to 8 to 13 and the mixture is stirred, etc. On this occasion, a reaction temperature is preferably 0 to 300° C., more preferably 10 to 200° C., and a reaction pressure is not particularly limited.

EXAMPLES

Next, the present invention is explained more specifically by referring to Examples, although the scope of the present invention is not limited by these.

Reference Example A1

Synthesis of 4,5-dihydroxy-2-imidazolidinone Compound

In a 1000 ml glass vessel equipped with a stirrer, thermometer and a dropping funnel were charged 290 g (2.0 mol) of 40 wt % aqueous glyoxal solution and triethylamine (a pH of the reaction mixture represented 9). Then, while maintaining the liquid temperature to 25 to 35° C., a solution in which 176 g (2.0 mol) of 1,3-dimethylurea had been dissolved in 176 ml of water was gradually added to the mixture, and then, the mixture was reacted at the same temperature for 15 hours under stirring to obtain 666.6 g of an aqueous solution A containing 4,5-dihydroxy-1,3-dimethyl-2-imidazolidinone.

To 333.3 g of the aqueous solution A was added 700 ml of diethyl carbonate, and the mixture was concentrated under reduced pressure (inner temperature 40 to 60° C., vapor temperature 40 to 60° C., 13 to 2 kPa). The obtained white solid was collected by filtration, dried at 50° C. under reduced pressure to obtain 137 g (Isolation yield based on 1,3-dimethylurea; 88.3%) of 4,5-dihydroxy-1,3-dimethyl-2-imidazolidinone with purity of 94.1% (absolute quantitative value by high-performance liquid chromatography).

Physical properties of the 4,5-dihydroxy-1,3-dimethyl-2-imidazolidinone are shown below.

$^1$H-NMR (DMSO-D$_6$, δ (ppm)); 2.62 (6H, s), 4.74 (2H, s), 5.5 (2H, brs)

CI-MS (m/e); 147 (M+1)

Example A1

Synthesis of imidazolidin-2,4-dione Compound

In a 30 ml glass vessel equipped with a stirrer, thermometer and a reflux condenser were charged 1.0 g (6.8 mmol) of 4,5-dihydroxy-1,3-dimethyl-2-imidazolidinone synthesized in the same manner as in Reference example A1, 2 ml of water and 0.18 g (1.8 mmol) of 98% sulfuric acid, and the mixture were reacted at 95 to 100° C. for 6 hours. After completion of the reaction, the reaction mixture was analyzed by high-performance liquid chromatography (quantitative value by refractive index detector), then, 766 mg (Reaction yield; 87%) of 1,3-dimethylimidazolidin-2,4-dione was formed.

Example A2

Synthesis of imidazolidin-2,4-dione Compound

Reaction was carried out in the same manner as in Example A1 except for changing the acid catalyst to 0.15 g (1.54 mmol) of methanesulfonic acid in Example A1. As a result, 800 mg (Reaction yield; 91%) of 1,3-dimethylimidazolidin-2,4-dione was formed.

Example A3

Synthesis of imidazolidin-2,4-dione Compound

Reaction was carried out in the same manner as in Example A1 except for changing the acid catalyst to 0.1 g of a sulfonic acid type cation exchange resin (trade name; DOWEX 50WX2) in Example A1. As a result, 766 mg (Reaction yield; 88%) of 1,3-dimethylimidazolidin-2,4-dione was formed.

Example A4

Synthesis of imidazolidin-2,4-dione Compound

Reaction was carried out in the same manner as in Example A1 except for using 2 ml of 1,3-dimethyl-2-imidazolidinone as a solvent and changing the reaction temperature to 150° C., and the reaction time to 2 hours in Example A1. As a result, 877 mg (Reaction yield; 100%) of 1,3-dimethylimidazolidin-2,4-dione was formed.

Example A5

Synthesis of imidazolidin-2,4-dione Compound

Reaction was carried out in the same manner as in Example A4 except for changing the acid catalyst to 0.1 g of a sulfonic acid type cation exchange resin (trade name; DOWEX 50WX2) in Example A4. As a result, 739 mg (Reaction yield; 84.2%) of 1,3-dimethylimidazolidin-2,4-dione was formed.

Example B1

Synthesis of imidazolidin-2,4-dione Compound

In a 200 ml glass vessel equipped with a stirrer, thermometer, a dropping funnel and a distillation unit were charged 60 g (0.41 mol) of 4,5-dihydroxy-1,3-dimethyl-2-imidazolidinone and 60 ml of water. And then, the mixture was reacted at 100° C. to 200° C. for 2 hours while removing water under normal pressure by distillation. The obtained residue was evaporated under reduced pressure (109 to 117° C./0.53 to 0.67 kPa) to obtain 41 g (Isolation yield; 78%) of 1,3-dimethylimidazolidin-2,4-dione as a pale yellow liquid.

Physical properties of the obtained 1,3-dimethylimidazolidin-2,4-dione were as follows.

$^1$H-NMR (DMSO-D$_6$, δ/ppm); 2.83 (3H, s), 2.85 (3H, s), 3.93 (2H, s)

CI-MS (m/e); 129 (M+1)

Example C1

Synthesis of imidazolidin-2,4-dione Compound

In a 1000 ml glass vessel equipped with a stirrer, thermometer, a dropping funnel and a distillation unit was charged 290 g (2.0 mol) of 40 wt % aqueous glyoxal solution. And then, triethylamine is added thereto to prepare a basic mixed solution (At this time, the solution had a pH of 9). To the mixed solution was gradually added dropwise a solution comprising 176 g (2.0 mol) of 1,3-dimethylurea and 176 ml of water while maintaining a liquid temperature to 25 to 35° C. After stirring the solution at room temperature for 3 hours, the mixture was reacted by elevating the temperature to 200° C. over 2 hours while removing triethylamine and water under normal pressure by distillation. After completion of the reaction, the obtained reaction mixture was distilled under reduced pressure (105 to 107° C./0.67 to 1.33 kPa) to obtain 217 g (Isolation yield; 85%) of 1,3-dimethylimidazolidin-2,4-dione as a pale yellowish liquid.

Physical properties of the obtained 1,3-dimethylimidazolidin-2,4-dione were as follows.

$^1$H-NMR (300 MHZ, DMSO-D$_6$, δ (ppm)); 2.83 (3H, s), 2.85 (3H, s), 3.93 (2H, s)

CI-MS (m/e); 129 (M+1)

Reference Example D1

Synthesis of Aqueous Solution Containing 4,5-dihydroxy-2-imidazolidinone Compound In a 1000 ml glass vessel equipped with a stirrer, thermometer and a dropping funnel were charged 290 g (2.0 mol) of 40 wt % aqueous glyoxal solution and triethylamine a pH of the reaction mixture represented 9). Then, while maintaining the liquid temperature to 25 to 35° C., a solution in which 176 g (2.0 mol) of 1,3-dimethylurea had been dissolved in 176 ml of water was gradually added to the mixture, and then, the mixture was reacted at the same temperature for 3 hours under stirring, to obtain 611.4 g of an aqueous solution containing 4,5-dihydroxy-1,3-dimethyl-2-imidazolidinone.

Example D1

Acquisition of Solid State 4,5-dihydroxy-2-imidazolidinone Compound

To 100 g of the aqueous solution obtained in Reference example D1 was added 200 ml of 1,2-diethoxyethane and water was subjected to azeotropic distillation. The obtained white solid was 4,5-dihydroxy-1,3-dimethyl-2-imidazolidinone (Acquired amount; 27.5 g, Isolation yield based on 1,3-dimethylurea of Reference example D1; 53%), with purity of 93% (absolute quantitative value detected by high-performance liquid chromatography).

Example D2

Acquisition of Solid State 4,5-dihydroxy-2-imidazolidinone Compound

Reaction was carried out in the same manner as in Example D1 except for changing 1,2-diethoxyethane to diethyl carbonate in Example D1. The obtained white solid was 4,5-dihydroxy-1,3-dimethyl-2-imidazolidinone with purity of 94.7% (absolute quantitative value detected by high-performance liquid chromatography). (Acquired amount; 45.27 g, Isolation yield based on 1,3-dimethylurea of Reference example D1; 90%)

Example D3

Acquisition of Solid State 4,5-dihydroxy-2-imidazolidinone Compound

Reaction was carried out in the same manner as in Example D1 except for changing 1,2-diethoxyethane to anisole in Example D1. The obtained white solid was 4,5-dihydroxy-1,3-dimethyl-2-imidazolidinone with purity of 81.0% (absolute quantitative value detected by high-performance liquid chromatography). (Acquired amount; 38.71 g, Isolation yield based on 1,3-dimethylurea of Reference example D1; 65.6%)

Example D4

Acquisition of Solid State 4,5-dihydroxy-2-imidazolidinone Compound

Reaction was carried out in the same manner as in Example D1 except for changing 1,2-diethoxyethane to butyl acetate in Example D1. The obtained white solid was 4,5-dihydroxy-1,3-dimethyl-2-imidazolidinone with purity of 94.6% (absolute quantitative value detected by high-performance liquid chromatography). (Acquired amount; 26.26 g, Isolation yield based on 1,3-dimethylurea of Reference example D1; 52.0%)

Example D5

Acquisition of Solid State 4,5-dihydroxy-2-imidazolidinone

To 333.3 g of the aqueous solution A obtained in Reference example A1 was charged 700 ml of diethyl carbonate, and water was subjected to azeotropic distillation. The obtained white solid was 4,5-dihydroxy-1,3-dimethyl-2-imidazolidinone (Acquired amount; 137 g, Isolation yield based on 1,3-dimethylurea of Reference example A1; 88.3%) with purity of 94.1% (absolute quantitative value detected by high-performance liquid chromatography).

Example D6

Acquisition of Solid State 4,5-dihydroxy-2-imidazolidinone

To 333.3 g of the aqueous solution A obtained in Reference example A1 was charged 700 ml of butyl acetate, and water was subjected to azeotropic distillation. The obtained white solid was 4,5-dihydroxy-1,3-dimethyl-2-imidazolidinone (Acquired amount; 133.18 g, Isolation yield based on 1,3-dimethylurea of Reference example A1; 81.7%) with purity of 89.6% (absolute quantitative value detected by high-performance liquid chromatography).

The imidazolidin-2,4-dione compound prepared by the present invention is a useful compound, for example, as a material for decomposing a harmful halogenated aromatic hydrocarbon compound such as dioxin, etc., an electroless silver plating solution for electronic parts, or a diazo copying material, etc.

According to the present invention, an industrially suitable process for preparing an imidazolidin-2,4-dione compound, which is safe, simple and easy to prepare the imidazolidin-2,4-dione compound with high yield, can be provided.

Also, according to the present invention, a solid state 4,5-dihydroxy-2-imidazolidinone compound can be acquired from an aqueous solution containing a 4,5-dihydroxy-2-imidazolidinone compound. The 4,5-dihydroxy-2-imidazolidinone compound is useful as a synthetic intermediate or a starting material of medicines and agricultural chemicals.

The invention claimed is:

1. A process for preparing an imidazolidin-2,4-dione compound represented by the formula (2):

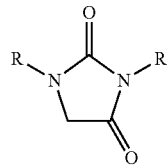

wherein R represents a hydrogen atom or hydrocarbon group, which comprises subjecting a 4,5-dihydroxy-2-imidazolidinone compound represented by the formula (1):

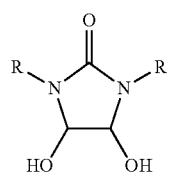

wherein R has the same meaning as defined above, to dehydration reaction in the presence of an acid catalyst(s).

2. The process according to claim 1, wherein the acid catalyst(s) is at least one acid selected from the group consisting of sulfonic acids, hydrogen halides, halogenated carboxylic acids, clay minerals, sulfonic acid type cation exchange resins, fluorinated sulfonic acid resins, silica-alumina and inorganic oxides.

3. The process according to claim 1 or 2, wherein an amount of the acid catalyst(s) to be used is 0.01 to 1000 mg based on 1 g of the 4,5-dihydroxy-2-imidazolidinone compound.

4. The process according to claim 1, wherein the 4,5-dihydroxy-2-imidazolidinone compound represented by the formula (1) is a material obtained by subjecting a urea compound represented by the formula (3):

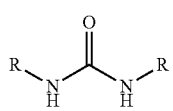

wherein R represents a hydrogen atom or hydrocarbon group,
and glyoxal to condensation reaction in the presence of a base.

5. A process for preparing an imidazolidin-2,4-dione compound represented by the formula (2):

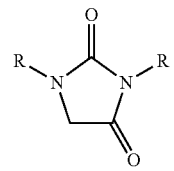

wherein R represents a hydrogen atom or hydrocarbon group, which comprises reacting a mixed solution containing a urea compound represented by the formula (3):

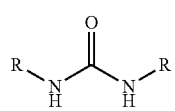

wherein R has the same meaning as defined above,
glyoxal and a base at 20 to 300° C.

6. The method according to claim 5, wherein the reaction is carried out after adding the urea compound represented by the formula (3) to a mixed solution of glyoxal and a base.

7. The method according to claim 6, wherein the mixed solution of glyoxal and a base is basic.

8. The method according to any one of claims 5 to 7, wherein the base is an organic base.

9. The method according to claim 8, wherein the reaction is carried out while removing the organic base and water by distillation.

10. A method of acquiring a solid state 4,5-dihydroxy-2-imidazolidinone compound represented by the formula (1):

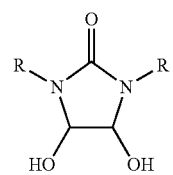

wherein R represents a hydrogen atom or a hydrocarbon group;

which comprises mixing an organic solvent with an aqueous solution containing a 4,5-dihydroxy-2-imidazolidinone compound represented by the formula (1), and subjecting the mixture to azeotropic distillation.

11. The acquiring method according to claim 10, wherein the aqueous solution containing the 4,5-dihydroxy-2-imidazolidinone compound represented by the formula (1) is an aqueous solution obtained by reacting a urea compound represented by the formula (3):

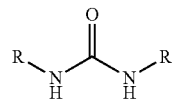

(3)

wherein R represents a hydrogen atom or a hydrocarbon group,
and glyoxal in the presence of a base(s).

12. The acquiring method according to claim 11, wherein the base(s) is an organic amine(s).

13. The acquiring method according to any one of claims 10 to 12, wherein the organic solvent forms an azeotropic mixture with water at 1 to 100 kPa and 30 to 130° C.

14. The process according to any one of claims 1 to 2, wherein the reaction is carried out at 100° C. to 300° C.

15. The process according to claim 14, wherein the reaction is carried out in water at an initial stage of the reaction.

* * * * *